United States Patent [19]

Epstein et al.

[11] 4,090,084
[45] May 16, 1978

[54] MAMMOGRAPHY COMPRESSION APPARATUS

[76] Inventors: Heywood Y. Epstein, 250 E. 65th St., New York, N.Y. 10021; Carmine Famiglietti, 37 Lynton Rd., Albertson, N.Y. 11507

[21] Appl. No.: 771,435

[22] Filed: Feb. 24, 1977

[51] Int. Cl.² .............................................. G03B 41/16
[52] U.S. Cl. ................................ 250/439 R; 250/451; 250/505
[58] Field of Search ............... 250/439 R, 444, 445 R, 250/451, 456, 505

[56] References Cited

U.S. PATENT DOCUMENTS

| 3,365,575 | 1/1968 | Strax | 250/445 |
|---|---|---|---|
| 3,578,971 | 5/1971 | Lasky | 250/456 |
| 3,609,355 | 9/1971 | Schwarzer | 250/445 |
| 3,991,316 | 11/1976 | Schmidt | 250/439 R |

FOREIGN PATENT DOCUMENTS 238,079  2/1969  U.S.S.R. ................................. 250/505

Primary Examiner—Craig E. Church
Attorney, Agent, or Firm—M. Ted Raptes; Reuben Epstein

[57] ABSTRACT

This invention relates to a mammography apparatus and more particularly to the means for compressing a pressure plate of the apparatus against the breast. The mounting of the pressure plate is such that the pressure can be applied uniformly throughout the breast area. To enable such uniform pressure to be obtained, the pressure plate is connected at its opposite ends to slide means which slide on tracks mounted on the cone of the X-ray machine. For the determination of the thickness of the compressed breast tissue between the pressure plate and the film upon which the breast rests, a measuring rod is secured to the tracks and a pointer is attached to the means which move on the tracks.

5 Claims, 10 Drawing Figures

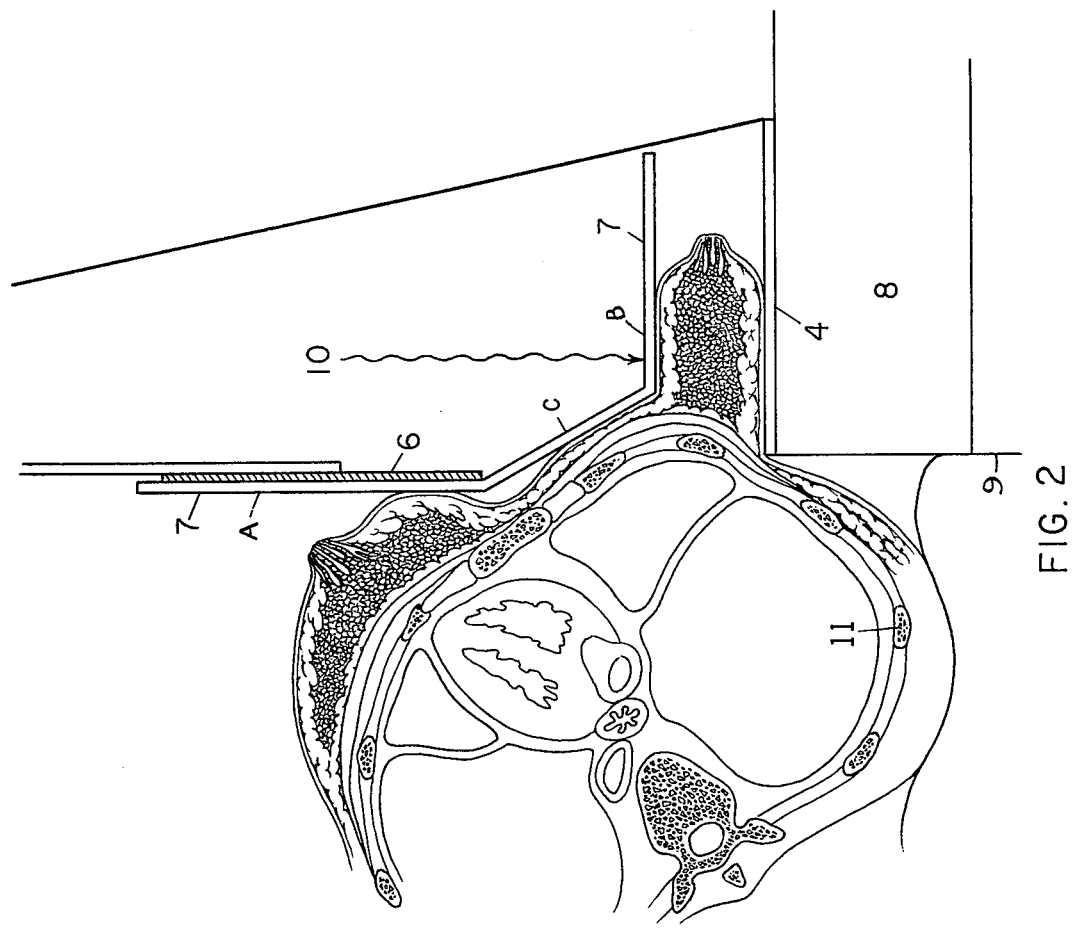
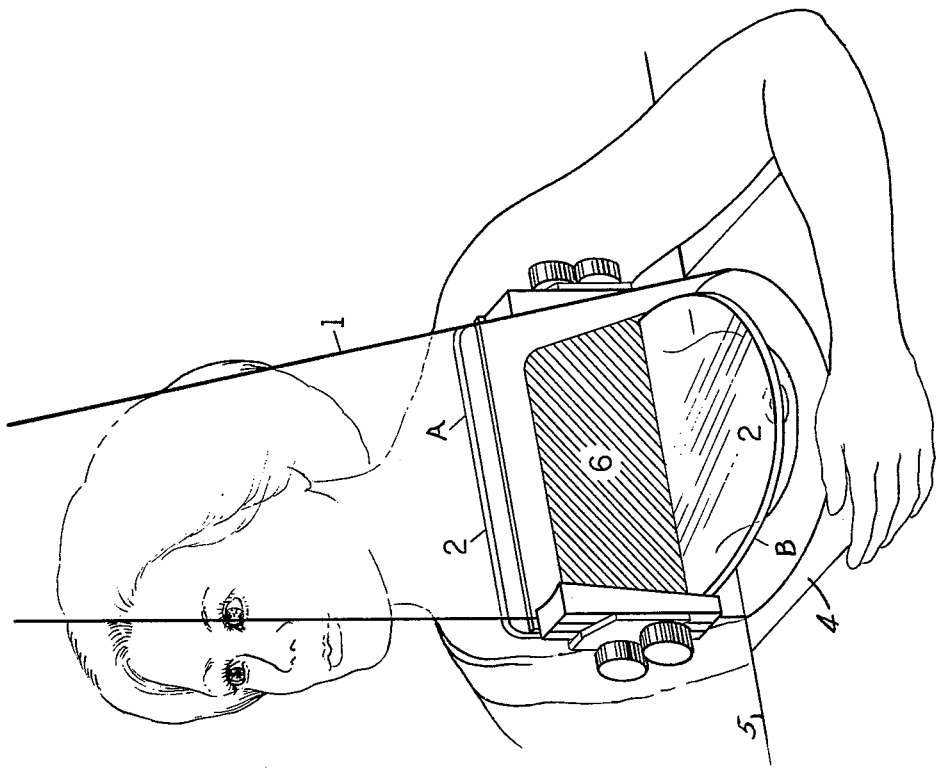
FIG. 2
FIG. 1

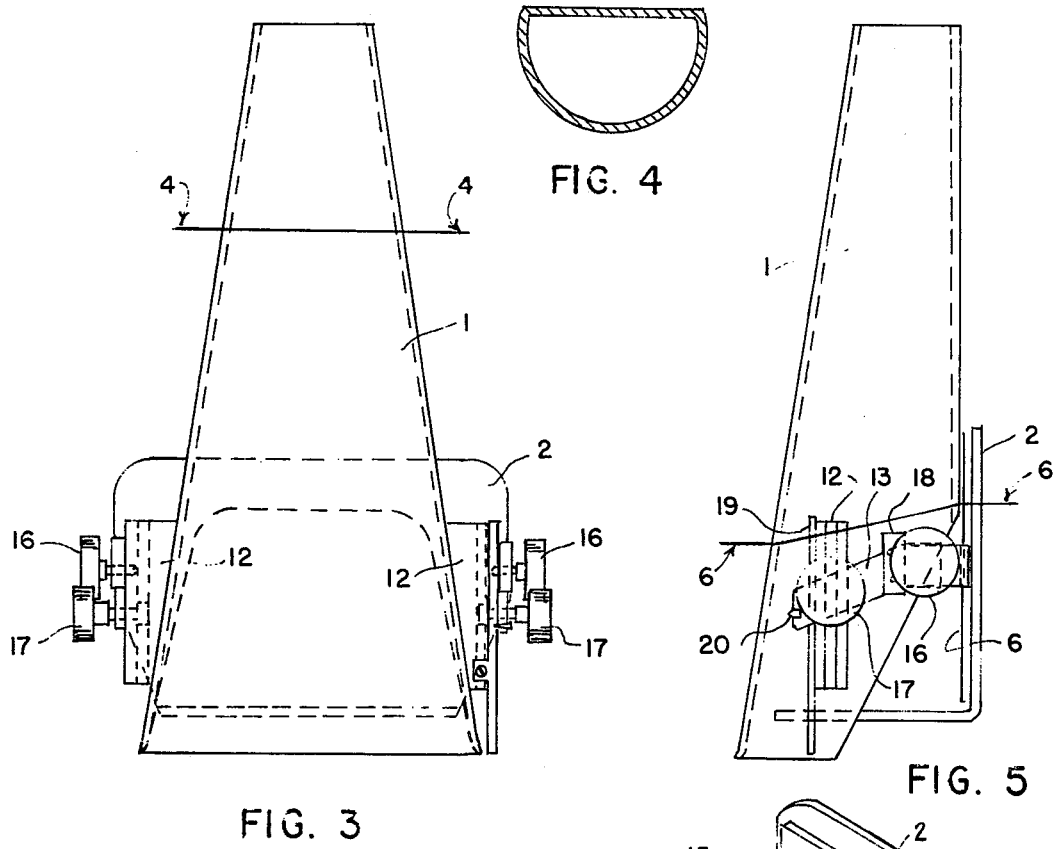
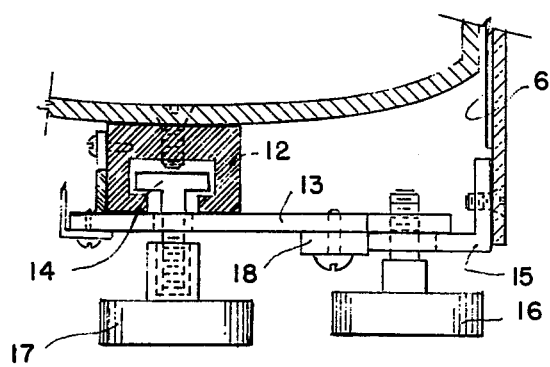
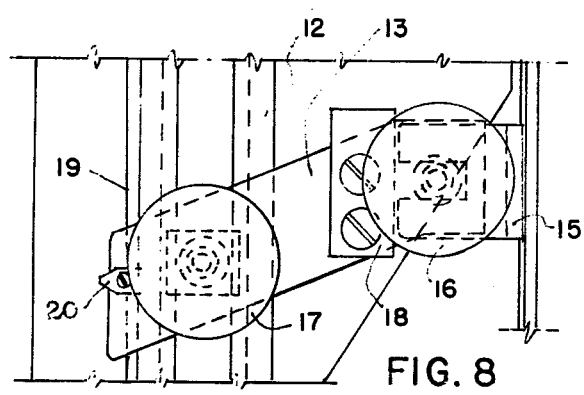
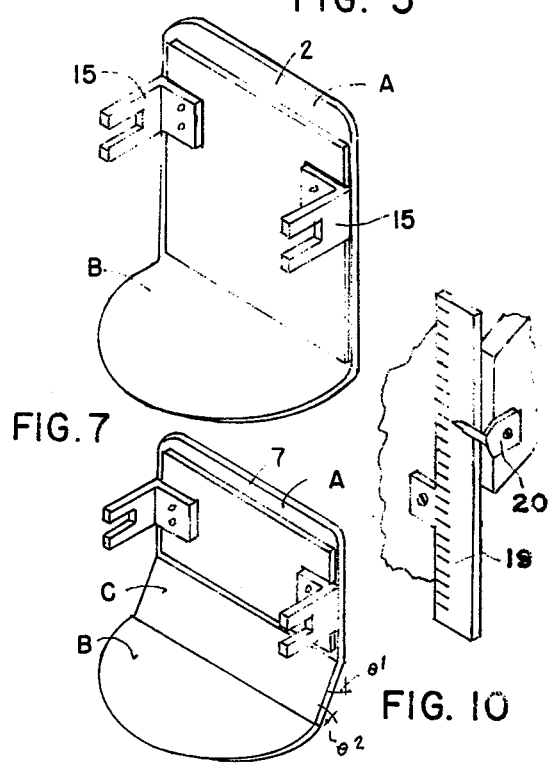

MAMMOGRAPHY COMPRESSION APPARATUS

BACKGROUND OF THE INVENTION

This invention relates to the means for taking X-ray pictures of the breast. In the present practice of taking such X-ray pictures, it is desirable to apply compression to the breast, the X-ray picture thereby being improved. Various means have been devised, such as a balloon, for the application of the pressure. In U.S. Pat. No. 3,824,397, another such means is shown wherein the pressure is applied to a plastic sheet which is placed on the breast, such means, however, do not provide the application of the pressure uniformly over the entire breast. As a result of applying the pressure irregularly, the image is not improved in all areas of the breast.

BRIEF SUMMARY OF THE INVENTION

An object of the present invention is to provide means for applying uniform pressure to the entire breast so that a properly collimated, optimal X-ray picture encompassing all the tissue of interest can be obtained.

A further object of the invention is to provide means whereby the final tissue thickness can be measured. A basis for comparison is thereby available when a follow-up picture is taken. Exposure factors can be taken from a table of tissue thickness reducing the need for retakes. The novel mammographic compression apparatus described herein results in:

(a) improved diagnostic quality of the resulting radiographic images by uniform compression and demonstration of ribs in the lateral view while maintaining compression;

(b) reduced patient radiation exposure by enabling use with long target-film distance systems, providing additional lucite filtration and collimating of the X-ray beam to the tissues being compressed and (c) great economies due to inexpensive modifications as opposed to replacement of major or large componets.

BRIEF DESCRIPTION OF THE DRAWINGS

FIG. 1 is a perspective view of the cone of an X-ray machine, the pressure plate and radiation shield of a first selectable pressure plate means of the invention, and of the patient as the cranio-caudal mammogram is being taken. For this exposure the patient is in the seated position. In this view, the metallic cone is depicted as transparent so that the parts within the cone are visible.

FIG. 2 is a cross-section of the chest and breasts of a patient, and of a modified pressure plate, and radiation shield of a second selectable pressure plate means when the lateral mammogram is being taken of one breast with the patient lying on her side.

FIG. 3 is a front elevational view of the cone with the pressure plate means mounted thereon.

FIG. 4 is a cross-section of the cone taken on line 4—4 of FIG. 3.

FIG. 5 is a side elevational view of the cone with the first selectable pressure plate means mounted thereon.

FIG. 6 is an enlarged fragmentary cross-sectional view taken on line 6—6 of FIG. 5.

FIG. 7 is a perspective view of the first selectable pressure plate means used in the embodiment of FIG. 1.

FIG. 8 is an enlarged, fragmentary elevational side view of the pressure plate mounting means shown in FIGS. 5 and 6.

FIG. 9 is a perspective view of the second selectable pressure plate means used in the embodiment of FIG. 2.

FIG. 10 is a perspective view of the pointer and measuring rod arrangement.

DETAILED DESCRIPTION OF THE INVENTION

FIG. 1 shows the patient with the breast in position and facing the cone 1 through which the X-rays pass from an X-ray machine, not shown. The lower part of the cone 1, at the side facing the patient, is cut away, as in some prior devices, to provide an opening for the placing of the breast within the hollow cone 1. In the present device, the opening of cone 1 has been made larger than usual to provide additional space for the insertion of a first selectable pressure plate 2 within the hollow cone 1 when the craniocaudal mammogram is to be taken and for the insertion of a second selectable pressure plate 7 when the lateral view mammogram is to be taken. Cone 1 is generally conical, but is flat on the side facing the patient (see FIG. 5). The pressure plate 2 is mounted on cone 1, and vertical portion A is pressed into contact with the chest and horizontal portion B into contact with the breast 3 of the patient. Both the horizontal portion B of the pressure plate and the breast 3 of the patient extend into the confines of the cone 1. The cone 1 is of metal as in prior apparatus and the pressure plate 2 is preferably of plastic, for example, lucite. The pressure plate 2 is movably mounted on the cone 1 in a manner to enable the lower horizontal portion B of the pressure plate to uniformly compress the breast 3. As seen in FIGS. 3, 5 and 6, the pressure plate 2 is mounted on the external surface of cone 1 for movement of both the vertical portion A and the horizontal portion B vertically, with the vertical portion A movable along the flat side of cone 1. The breast 3 and lower edge of cone 1 rest on the casette 4 which contains the X-ray film, thus establishing a final repeatable target-film distance. The casette 4 is placed on a table of other support 5. In front of the vertical portion A of the pressure plate 2 there is mounted in contact therewith a radiation shield 6 to protect the patient from the radiation. The provision of the shield 6 on the vertical portion A of pressure plate 2 extending to the bend between portion A and portion B provides maximum collimation of the X-ray beam. The patient exposure to useless penumbra is minimized while the breast receives the collimated beam with minimum adulteration by scatter radiation.

In the embodiment of FIG. 2, where the patient is lying on her side, a pressure plate 7 of slightly different shape than that of pressure plate 2, is used. The means for mounting pressure plate 7 is the same as that for pressure plate 2. Pressure plate 7 has a vertical portion A, a horizontal portion B, and an inwardly inclined portion C between the other two portions. This shape provides a close contact with the chest and breast of the patient when the patient is lying on her side. As in the FIG. 1 embodiment, a radiation shield 6 is placed in front of pressure plate 7 and the breast 3 rests on a casette 4 containing the X-ray film therein. The casette 4 is disposed on support 8 placed on table 9. In this embodiment, the X-ray 10, in addition to producing an image of the breast, also project the image of the ribs 11 onto the edge of the film contained within the casette 4. By this means the patient is shielded from penumbra, the film receives minimum scatter radiation, the edge of the rib cage is imaged, confirming proper position, while simultaneously the breast is uniformly compressed.

FIG. 3 shows the mounting of the pressure plate 2 on cone 1, as seen from the front curved side of cone 1. The pressure plate is mounted on the flat, rear side of cone 1 with the vertical portion A of pressure plate 2 in contact with the chest of the patient and the horizontal B portion in contact with the breast. For mounting the pressure plate 2 on cone 1, the cone is provided with tracks 12 which are placed on both sides of cone 1.

As shown in FIGS. 5 and 6, pressure plate 2 is connected by links 13 to a slidable member 14 (see FIG. 6), for movement up and down on track 12 thereby moving pressure plate 2 for application of pressure to the breast. The pressure plate 2 is connected to link 13 by knobs 16 which pass through brackets 15 on pressure plate 2 (see FIG. 6). Knobs 16 are in threaded engagement with link 13. Slidable member 14 passes through an opening in link 13 and is in threaded engagement with knob 17. Knob 17 can be used to move the slidable member 14 up and down and by rotating it can hold the slidable member 14 in fixed position. To more securely hold the link 13 and slidable member 14 in fixed position, with respect to the pressure plate 2, a block member 18 is secured to link 13 adjacent the brackets 15 of the pressure plate. FIG. 7 shows the pressure plate 2 having the vertical portion A, the horizontal portion B, with brackets 15 mounted at each side of the vertical portion A. The radiation shield 6 is in front of the vertical portion A.

FIG. 8 shows the measuring rod 19 positioned adjacent the track member 12 and the pointer 20 secured to the link 13. By reading the position of the pointer 20 on the measuring rod 19, one can determine the thickness of the breast tissue between the horizontal portion B of the pressure plate 2 and the X-ray film.

FIG. 9 shows the pressure plate 7 used in obtaining the so-called lateral view of the breast. The pressure plate 7 has the vertical portion A and horizontal portion B as in pressure plate 2, but includes also an inwardly inclined portion C between those two portions for allowing the rib cages to fall within the X-ray beam and assure the examiner that the entire breast has been included in the film. Suitable angles for the inclined portion C are $\theta_1$ of 30° and $\theta_2$ of 60°.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Mammography apparatus comprising:
   A. a hollow metallic member for passage therethrough of X-rays from an X-ray source, said hollow member having a generally conical shape and a substantially flat side, said flat side containing an aperture in the lower part thereof to permit positioning of a woman's breast within said hollow member;
   B. first selectable pressure plate means comprising a vertical portion shielded against X-rays and a horizontal portion transparent to X-rays, said first pressure plate means being movably mounted on said hollow member with said vertical portion being movable vertically externally of said hollow member along said flat wall of said hollow member, said horizontal portion being movable vertically within the confines of said hollow member for application of pressure to said breast positioned within said hollow member, the chest of the woman facing the vertical portion of said first pressure plate while the mammogram is being taken and pressure is being applied against the breast;
   C. means for movably mounting said first pressure plate means on said hollow member comprising: track means on the external surface of the sides of said hollow member, movable means on said tracks, means for attaching said first pressure plate means to said movable means, and means for fixedly holding said movable means on said track means;
   D. cassette means containing film upon which said hollow member rests and upon which said breast is to be placed; said arrangement of cassette means and hollow member providing a long fixed target-film distance between said X-ray source and said film.

2. The apparatus of claim 1 wherein measuring rod means is positioned adjacent a track member and pointer means is secured to said movable means.

3. The apparatus of claim 1 wherein a second selectable pressure plate means is used in place of said first selectable pressure plate means, said second selectable pressure plate means having a vertical portion shielded against X-rays, a horizontal portion, and an inclined portion between said vertical and horizontal portions, said horizontal and inclined portions being transparent to X-rays, said inclined portion allowing the rib cages of the woman to fall within the X-ray beam when a lateral view mammogram is being taken.

4. Mammography apparatus comprising:
   A. a hollow metallic member for passage therethrough of X-rays from an X-ray source, said hollow member being of generally conical shape and having a substantially flat side which has an aperture in the lower part of said flat side to permit positioning of the breast within said hollow member;
   B. first selectable pressure plate means having a vertical portion shielded against X-rays and a horizontal portion transparent to X-rays, said pressure plate means being movably mounted on said hollow member with said vertical portion movable vertically externally of said hollow member along the flat wall of said hollow member, and the horizontal portion movable vertically within the confines of the hollow member for application of pressure to the breast of a woman positioned within the hollow member, the chest of the woman facing the vertical portion of said pressure plate when pressure is being applied against the breast and the mammogram is to be taken, said pressure plate means having attachment means at its sides for attachment to means for moving it;
   C. means mounted at the sides of said hollow member for attachment to the sides of the pressure plate means and for vertically moving said pressure plate means, and means for securing said movable member in a fixed position, and
   D. cassette means containing film upon which said hollow member rests, and upon which said breast is to be placed, said arrangement of cassette means and hollow member providing a long fixed target-film distance between said X-ray source and said film.

5. The apparatus of claim 4 wherein a second selectable pressure plate means is used in place of said first selectable pressure plate means, said second selectable pressure plate means having a vertical portion shielded against X-rays, a horizontal portion, and an inclined portion between the vertical and horizontal portions, said horizontal and inclined portions being transparent to X-rays, the inclined portion allowing the rib cages of said woman to fall within the X-ray beam when a lateral view mammogram is being taken.

* * * * *